(12) United States Patent
Schild et al.

(10) Patent No.: US 6,488,670 B1
(45) Date of Patent: Dec. 3, 2002

(54) CORRUGATED ABSORBENT SYSTEM FOR HYGIENIC PRODUCTS

(75) Inventors: Lisa A. Schild, Roswell, GA (US); Jaime Braverman, Alanta, GA (US); Jai L. Jones, Lawrenceville, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 107 days.

(21) Appl. No.: 09/699,168

(22) Filed: Oct. 27, 2000

(51) Int. Cl.$^7$ ............................................. A61F 13/15
(52) U.S. Cl. ............ 604/385.24; 604/378; 604/385.01; 604/354
(58) Field of Search ............................. 604/354, 385.01, 604/378, 385.24

(56) References Cited

U.S. PATENT DOCUMENTS

| | | |
|---|---|---|
| 3,338,992 A | 8/1967 | Kinney |
| 3,341,394 A | 9/1967 | Kinney |
| 3,481,337 A | 12/1969 | Ruffo ........................ 128/284 |
| 3,502,763 A | 3/1970 | Hartmann |
| 3,542,615 A | 11/1970 | Dobo et al. |
| 3,683,917 A | 8/1972 | Comerford |
| 3,692,618 A | 9/1972 | Dorschner et al. |
| 3,802,817 A | 4/1974 | Matsuki et al. |
| 4,100,324 A | 7/1978 | Anderson et al. |
| 4,111,733 A | 9/1978 | Periers |
| 4,232,674 A | 11/1980 | Melican |
| 4,340,563 A | 7/1982 | Appel et al. |
| 4,413,032 A | 11/1983 | Hartmann et al. |
| 4,488,928 A | 12/1984 | Ali Khan et al. |
| 4,578,070 A | 3/1986 | Holtman ...................... 604/378 |
| 4,685,914 A | 8/1987 | Holtman ...................... 604/368 |

(List continued on next page.)

FOREIGN PATENT DOCUMENTS

| | | | |
|---|---|---|---|
| EP | 0 525 676 A3 | 7/1992 | ............ A61F/13/15 |
| EP | 1 020 168 A1 | 7/2000 | ............ A61F/13/15 |
| FR | 2 504 799 | 5/1982 | ............ A61F/13/16 |
| WO | WO 94/09737 | 5/1994 | ............ A61F/13/15 |
| WO | 96/00545 | 1/1996 | |
| WO | WO 96/00625 | 1/1996 | ............ B20C/53/26 |
| WO | WO 00/36199 | 6/2000 | ............ D04H/1/70 |

OTHER PUBLICATIONS

Manson, John A. and Sperling, Leslie H., *Polymer Blends & Composites*, Plenum Press, a division of Plenum Publishing Corp., New York, New York, pp. 273–277 (1976).

*Primary Examiner*—John J. Calvert
*Assistant Examiner*—Angela J Grayson
(74) *Attorney, Agent, or Firm*—Pauley Petersen Kinne & Erickson

(57) ABSTRACT

An absorbent article having a fluid permeable top sheet, a fluid impermeable back sheet, and a corrugated absorbent material having a plurality of alternating peaks and valleys disposed between the fluid permeable top sheet and the fluid impermeable back sheet. The corrugated absorbent material can be a nonwoven web of a synthetic material or a web comprising natural fibers such as a pulp fibers, and include a binder and/or a superabsorbent material. The corrugated absorbent material can be formed by various processes, such as feeding the absorbent material through a nip having a doctor blade which reduces the speed of the absorbent material exiting the nip, thereby creating corrugations.

41 Claims, 3 Drawing Sheets

U.S. PATENT DOCUMENTS

| | | |
|---|---|---|
| 4,795,668 A | 1/1989 | Krueger et al. |
| 4,818,464 A | 4/1989 | Lau |
| 4,874,457 A * | 10/1989 | Swieringa .................. 156/474 |
| 4,885,204 A | 12/1989 | Bither et al. |
| 4,960,477 A | 10/1990 | Mesek |
| 5,037,409 A | 8/1991 | Chen et al. |
| 5,045,387 A | 9/1991 | Schmalz |
| 5,057,368 A | 10/1991 | Largman et al. |
| 5,069,970 A | 12/1991 | Largman et al. |
| 5,108,820 A | 4/1992 | Kaneko et al. |
| 5,108,827 A | 4/1992 | Gessner |
| 5,128,082 A | 7/1992 | Makoui |
| 5,167,740 A | 12/1992 | Michaelis et al. |
| 5,252,374 A | 10/1993 | Larsonneur |
| 5,277,976 A | 1/1994 | Hogle et al. |
| 5,318,554 A | 6/1994 | Young et al. |
| 5,336,552 A | 8/1994 | Strack et al. |
| 5,364,382 A * | 11/1994 | Latimer et al. ............. 604/378 |
| 5,382,400 A | 1/1995 | Pike et al. |
| 5,456,982 A | 10/1995 | Hansen et al. |
| 5,466,410 A | 11/1995 | Hills |
| 5,522,809 A | 6/1996 | Larsonneur |
| 5,540,992 A | 7/1996 | Marcher et al. |
| 5,558,924 A | 9/1996 | Chien et al. |
| 5,582,904 A | 12/1996 | Harrington |
| 5,728,083 A * | 3/1998 | Cohen ....................... 604/368 |
| 5,865,824 A | 2/1999 | Chen et al. |
| 5,976,665 A | 11/1999 | Hansson |

* cited by examiner

CORRUGATED ABSORBENT SYSTEM FOR HYGIENIC PRODUCTS

BACKGROUND OF THE INVENTION

Absorbent articles, such as diapers, child training pants, adult incontinence garments, swim wear, feminine pads and the like, typically include at least one liquid-permeable top layer for direct contact with the wearer, an absorbent core layer, and a substantially liquid-impermeable outer cover material. The absorbent core is positioned between the top layer(s) and the outer cover material. When the absorbent article is exposed to a liquid insult, liquid is absorbed through the top layer and deposited into the absorbent core for distribution and retention. The outer cover prevents the liquid in the absorbent core from leaving the product.

To perform its function, the absorbent core of an absorbent article should be capable of intaking large volumes of fluid rapidly, with some control. In this case, the absorbent material necessarily requires a large amount of void space to take in a fluid insult, but needs the appropriate structural characteristics in controlling, spreading and retaining the fluid.

PCT International Publication No. WO 96/00545 teaches a corrugated liquid permeable top layer disposed over a non-corrugated absorbent core, providing improved softness due to reduced contact with the user's body. Additionally, the corrugated cover material provides channels which move fluid along the length of the product. Similarly, U.S. Pat. No. 5,976,665 to Hansson describes a liquid permeable corrugated and apertured casing sheet for absorbent articles for reducing contact with the wearer's skin. An absorbent system that can handle large amounts of fluid, control fluid movement, provide integrity during use, and improve softness and dryness is desired, but, based upon the prior art, has not been achieved to date. It is the intention of this disclosure to describe such a system.

SUMMARY OF THE INVENTION

The invention disclosed and claimed herein is a corrugated absorbent material having a plurality of alternating peaks and valleys for use in absorbent articles, including, but not limited to, disposable diapers, child training pants, swim wear, adult incontinence garment, sanitary pads or tampons, bandages, wound dressings and the like. The corrugated material is incorporated into the absorbent articles as the absorbent core, or part of the absorbent core, disposed between the fluid permeable top sheet and the fluid impermeable back sheet, to achieve improved fluid intake performance. In accordance with one embodiment of this invention, the absorbent core is modified in conjunction with the fluid permeable top sheet so as to allow the fluid permeable top sheet to adapt to the shape of the corrugated absorbent, thereby improving contact between the layers. The corrugated absorbent material in accordance with this invention provides improved fluid intake due to the higher material surface area for fluid contact, void volume created by the corrugation process, a visual cue for improved fluid intake due to improved material aesthetics, improved absorption of fluids such as urine, menses, and bowel movement (BM) due to the surface structure of the material which provides "pockets" for intake, and softness and dryness due to the modified surface topography of the corrugated absorbent material providing reduced contact with the skin of the wearer. The softness attribute may also help with body conformance and fit in that the corrugated structure may allow for some stretch of the absorbent web.

BRIEF DESCRIPTION OF THE DRAWINGS

These and other features of this invention will be better understood from the following detailed description taken in conjunction with the drawings wherein.

DESCRIPTION OF PREFERRED EMBODIMENTS

Definitions

Figure 1A:
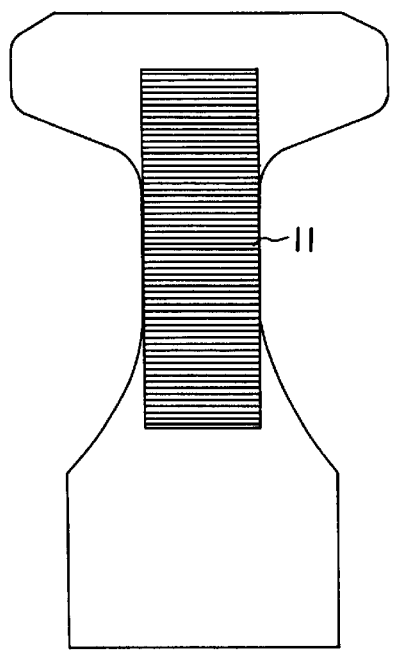
FIGS. 1a and 1b are diagrams showing a corrugated absorbent in accordance with this invention utilized as an intake layer in a dual layer diaper absorbent design.

As used herein, the term "comprising" is open and includes not only recited elements, components or steps, but also any additional elements, components or steps that do not prevent operation of the invention as described.

As used herein, the term "machine direction" refers to the direction of travel of the forming surface onto which fibers are deposited during formation of a nonwoven web.

As used herein, the term "cross-machine direction" refers to the direction perpendicular to the machine direction.

As used herein, the term "nonwoven web" or "nonwoven material" means a material having a structure of individual fibers or threads which are interlaid, but not in an identifiable manner, as in a knitted fabric. Nonwoven materials or webs have been formed from many processes such as, for example, spunbonding processes, meltblowing processes, and bonded carded web processes. The basis weight of nonwoven fabrics is usually expressed in grams per square meter (gsm) and the fiber diameters are usually expressed in microns.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 50 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes. A nonwoven web of spunbond fibers produced by melt spinning is referred to as a "spunbond".

As used herein, the term "bonded carded" or "bonded carded webs" refers to nonwoven webs formed by carding processes as are known to those skilled in the art and further described, for example, in U.S. Pat. No. 4,488,928 to Alikhan and Schmidt. Typically, carding processes involve starting with a blend of, for example, staple fibers with bonding fibers or other bonding components in a bulky batt that is combed or otherwise treated to provide a generally uniform basis weight. This web is heated or otherwise treated to activate the adhesive component, resulting in an integrated, usually lofty nonwoven material.

As used herein, the term "polymer" generally includes, but is not limited to, homopolymers, copolymers, such as for example, block, graft, random and alternating copolymers, terolymers, etc., and blends and modifications thereof. In addition, unless otherwise specifically limited, the term "polymer" includes all possible geometric configurafions of the material. The configurations include, but are not limited to, isotactic, atactic, syndiotactic, and random symmetries.

As used herein, the teri "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger, et al., U.S. Pat. No. 5,540,992 to Marcher et al., and U.S. Pat. No. 5,336,552 to Strack et al. Bicomponent fibers are also taught by U.S. Pat. No. 5,382,400 to Pike et al., and may be used to produce crimp in the fibers by using the differential rates of expansion and contraction of the two (or more) polymers. For two component fibers, the polymers are desirably present in ratios of 75/25 to 25/75 or any other desired ratio and, as an example, may be 50/50. Fibers formed of two or more segments of the same polymer, such as a polypropylene (PP)/PP fiber are considered to be monocomponent fibers.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation, New York, N.Y., IBSN 0-306-30831-2, at pages 273 through 277.

As used herein, the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "absorbent article" includes personal care absorbent articles such as disposable diapers, training pants, absorbent underpants, swim wear, adult incontinence products, feminine hygiene products, including sanitary pads and tampons, and the like, and bandages, wound dressings, wipes, and the like.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "stain" refers to fluid, wet or dry, which is present on the top surface, in, or on the bottom surface of a cover material or topsheet of an absorbent article.

The term "pulp" refers to fibers from natural sources such as woody and non-woody plants. Woody plants include, for example, deciduous and coniferous trees. Non-woody plants include, for example, cotton, flax, esparto grass, milkweed, straw, jute hemp, and bagasse.

The corrugated material of this invention provides the potential for benefits in fluid intake, the ability to z-direct fluid into a structure, and for conformance. The corrugated absorbent materials of this invention may also improve dryness by reducing contact with the skin and by improving cover desorption.

The corrugated material of this invention is a nonwoven material or system produced from a stabilized web, such as an airlaid composite comprising pulp, a binder and, in some cases, a superabsorbent. Pulp is useful in absorbent products, and generally constitutes about 1% to about 90% by weight of the composite nonwoven fabric used in such products. In accordance with one embodiment of this invention, the corrugated material comprises pulp in the range of about 75% to about 98% by weight of the total material weight. The pulp may be unrefined or may be beaten to various degrees of refinement. Small amounts of synthetic binding fibers, wet-strength resins and/or resin binders may be added to improve strength and abrasion resistance. Useful binders and wet-strength resins include, for example, T-255 thermal binder fiber available from Trevira, Kymene 557H available from Hercules Chemical Company and Parez 631 available from American Cyanamid, Inc. The corrugated material in accordance with this invention preferably comprises a binder in the range of about 2% to about 25% by weight of the total material weight. To provide resistance to z-direction compression so as to retain the corrugated structure and resultant material functionality over the life of the product, resilient fibers, or other structural means, may be incorporated into the structure to provide a level of resiliency.

Composite corrugated nonwoven materials in accordance with this invention may be produced by combining separate polymer and additive streams into a single deposition stream in forming the nonwoven webs. Such a process is taught, for example, by U.S. Pat. No. 4,100,324 to Anderson et al. which is hereby incorporated by reference. U.S. Pat. No. 4,818,464 to Lau discloses the introduction of superabsorbent material as well as pulp, cellulose, or staple fibers through a centralized chute in an extrusion die for combination with resin fibers in a nonwoven web. The pulp, staple fibers, or other material are added to vary the characteristics of the resulting web, for example, strength and absorbency. It is recognized that other absorbent materials may be used to achieve similar results, including pulp fluff, fluff and superabsorbent, fiber binders, or a combination thereof, or any material suitable for absorbing fluid.

In some absorbent articles, it may be desirable to include one or more superabsorbents in the absorbent layer. Such superabsorbents may be particulate or fibrous. When the corrugated material of this invention is employed in the absorbent layer of such articles, the desired composition of the corrugated material is in the range of about 25% to about 75% by weight pulp, in the range of about 2% to about 25% by weight binder and in the range of about 0% to about 50% by weight superabsorbent.

The basis weight of the corrugated materials utilized in the absorbent layers of absorbent articles in accordance with this invention is defined in terms of a base sheet basis weight, that is the basis weight of the nonwoven material prior to corrugation. Preferably, the base sheet basis weight of the corrugated material of this invention is in the range of about 50 gsm to about 900 gsm. To obtain the desired material and product performance, the base sheet basis weight is increased upon corrugation in the range of about 20% to about 150%, resulting in the corrugated material of this invention having a corrugated basis weight in the range of about 60 gsm to about 2250 gsm. As described above, this invention also defines corrugation of the cover material in the same manner. In this instance, the cover material should be corrugated with about the same degree of corrugation as the absorbent. The basis weight of the cover material before corrugation can range from about 10 to about 80 gsm and more preferably from about 15 to about 50 gsm.

An intermediate layer can be placed between the fluid permeable top sheet and absorbent material to improve the overall intake and flowback properties of the material. The structural characteristics of such a layer depend on the characteristics of the top layer and the absorbent material that has been chosen for the application. These parameters should include materials that, with some synergy, will be capable of desorbing the top layer at a fast rate and provide low reflux of fluid to the user's body.

Figure 3A:
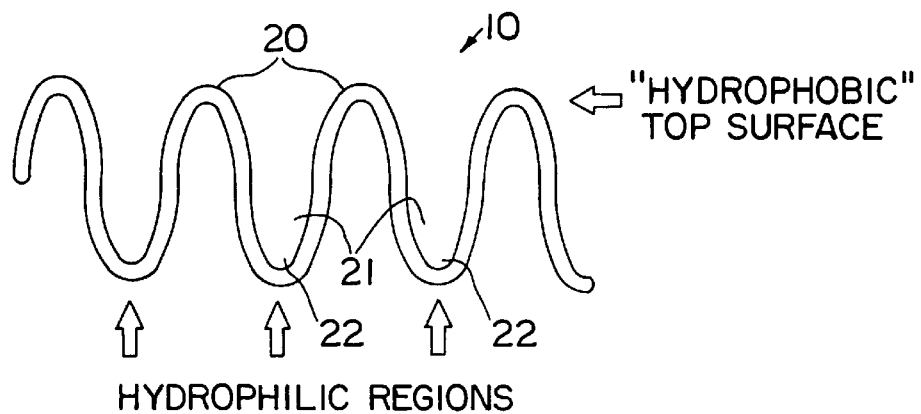
FIGS. 3a and 3b are diagrams showing a corrugated nonwoven absorbent structure in accordance with this invention comprising wettability gradients for enhanced fluid handling capability.
Figure 3B:
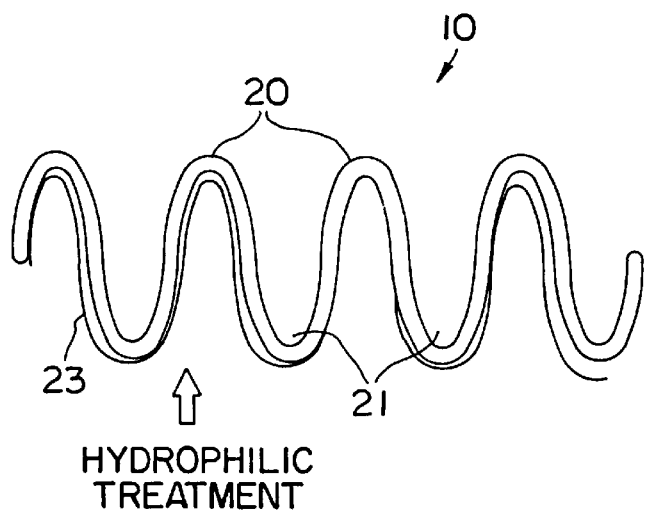
Figure 5:
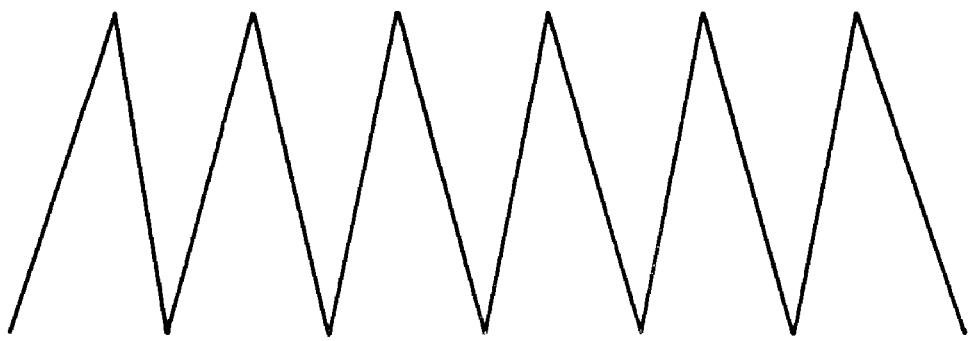
FIG. 5 is a diagram showing a corrugated nonwoven structure having triangular peaks and valleys in accordance with one embodiment of this invention.
Figure 6:
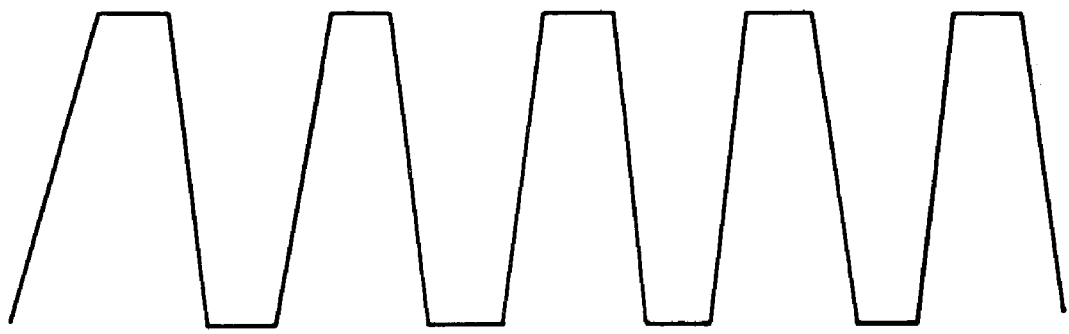
FIG. 6 is a diagram showing a corrugated nonwoven structure having peaks and valleys in the shape of plateaus.

As shown in FIGS. 3a and 3b, the corrugated material 10 of this invention comprises a plurality of alternating peaks 20 and valleys 21. To provide the desired absorbency properties, the frequency of peaks and valleys is preferably in the range of about one per 5 mm of material length to about one per 25 mm of material length. The desired thickness of the material is in the range of about 0.3 mm to about 25 mm. As shown in FIGS. 3a and 3b, the shape of the peaks 20 and valleys 21 is rounded. However, the peaks and valleys may have a triangular shape where they come to a sharp point such as shown in FIG. 5 or a plateau shape where the peaks and valleys are relatively flat as shown in FIG. 6. It will also be apparent that, for some applications, a combination of shapes may be desirable. Additionally, these corrugations may be zoned in the product and localized in strategic places for different functionality. For this reason, the combination of peak frequencies and heights may be varied depending upon the effect being pursued.

To promote rapid fluid intake by the corrugated nonwoven material and/or fluid permeable top layer used for this invention, it is desired that the surfaces of the material or the surface of the fibers forming the material be first wetted by the liquid. Wettability of nonwoven materials or fibers thereof is known to be achievable by treating the surface thereof with surfactants. See, for example, U.S. Pat. No. 4,413,032 to Hartmann et a l. and U.S. Pat. No. 5,045,387 to Schmalz. Alternative methods of imparting wettability to such materials are taught, for example, by U.S. Pat. No. 5,456,982 to Hansen et al. in which bicomponent fibers are provided with permanent hydrophilic surface properties by incorporating a surface active agent into the sheath component and optionally by including a hydrophilic polymer or copolymer in the sheath component. See also, U.S. Pat. No. 5,582,904 to Harrington which teaches the incorporation into a polyolefin-containing cast or spin-melt composition for production of nonwoven materials a modifier composition comprising at least one M, M-polyalkoxylate 10–22 carbon fatty acid amine, inclusive of amines having 12–20 carbons and preferably 18 carbon linear straight chain moiety corresponding to that found in stearic or oleic acid, and up to about 60%, including 0.1%–45% by weight of a modifier composition, of a primary or a secondary 10–22 carbon fatty acid amide, such as stearamide. A surfactant treatment system suitable for use in the corrugated material of this invention is a compound selected from the group consisting of ethoxylated hydrogenated fatty oils, monosaccharides, monosaccharide derivatives, polysaccharides, polysaccharide derivatives, and combinations thereof. Although a hydrophilic surface structure is desired for this invention, one which is hydrophobic is also feasible.

Fluid intake benefits may be enhanced by treating the corrugated material with a surfactant in a manner which produces wettability gradients within the material. An example of this feature is shown in FIG. 3a which shows application of the surfactant treatment, represented by reference numeral 22 to the valleys 21 of the corrugated structure 10 so as to aid in drawing fluid away from the peaks 20 (material surface), i.e. z-directed flow, of the corrugated structure. To further enhance the flow of fluid away from the material surface, the peaks 20 of the material may be designed to be hydrophobic. Similar functionality may also be achieved by applying a treatment 23 to the lower surface of the corrugated material 10 as shown in FIG. 3b. A wettability gradient for enhancement of fluid intake may also be effected by incorporating alternate raw materials, for example pulps with different wettability properties, in dual or multi-layered configurations.

As previously stated, absorbent articles in accordance with this invention typically include at least a liquid-permeable top layer for direct contact with the wearer, an absorbent core layer, and a substantially liquid-impermeable outer cover material. The absorbent core is positioned between the top layer and the outer cover material. It is important to note that a cover material not affixed to the absorbent core will have more difficulty absorbing fluid when a gap exists between layers. In accordance with one embodiment of this invention, the liquid-permeable top layer or cover is attached to the absorbent corrugated structure in a face-to-face relation, typically by a method selected from the group consisting of thermal bonding, powder bonding, adhesive bonding, entanglement, ultrasonics, and combinations thereof. In accordance with one embodiment, the fluid permeable top sheet has a surface topography corresponding to the shape of the corrugated absorbent material. The fluid permeable top layer may be a spunbond fabric or an apertured film and may include a bonded carded web sub-layer. The spunbond fabric may be made, for example, from monocomponent fibers, bicomponent fibers, biconstituent fibers or combinations thereof. In cases where product design does not permit such a layer to have connectivity with the absorbent system, it can be envisioned that pressure exerted by the user's body may provide such connectivity, thereby compensating for the lack of connectivity between layers and enabling fluid absorption.

Figure 1B:
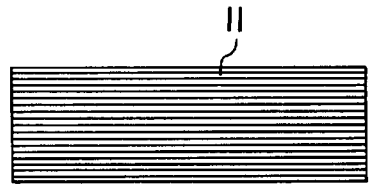

The corrugated nonwoven material of this invention may be employed in a variety of absorbent articles including, but not limited to, disposable diapers, training pants, swim wear, adult incontinence garments, feminine care products, such as sanitary pads and tampons, bandages and wound dressings. FIGS. 1a and 1b are drawings showing the corrugated absorbent material of this invention as an intake layer 11 in a dual layer diaper absorbent design. Depending upon the desired result, the corrugated material may be oriented in the disposable diaper with a machine direction orientation as shown in FIG. 1a or a cross direction orientation as shown in FIG. 1b. The cross direction orientation may provide additional protection against leakage by creating directional channels which force the fluid flowing into the absorbent layer to take a more elongated path along the length of the product. This configuration may also reduce stiffness in the crotch region of the product due to compressibility of the corrugated material in the cross direction.

Figure 2A:
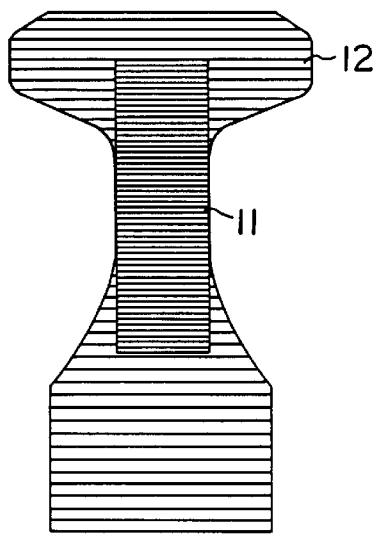
FIGS. 2a and 2b are diagrams showing a corrugated nonwoven material in accordance with this invention which may be applied to distribution/retention layers for desorption, dryness, and conformance improvements.
Figure 2B:
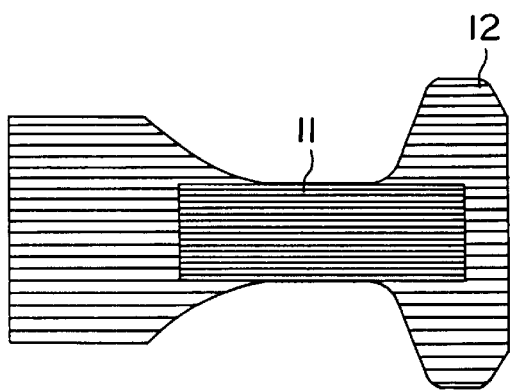

The use of the corrugated absorbent material of this invention is not limited to the fluid intake layers of the absorbent articles. It may also be applied to fluid distribution/retention layers 12 for desorption, dryness and conformance improvements. FIGS. 2a and 2b show examples of these types of structures where FIG. 2a corresponds to a machine direction corrugation orientation and FIG. 2b corresponds to a cross direction corrugation orientation. The absorbent structure of absorbent articles such as diapers may be fully corrugated for application to the total absorbent system of the diaper or it may be partially corrugated for, as an example, gender specific fluid intake applications. In the case of product use by males, the corrugated portion of the absorbent structure would be closer to the front of the diaper whereas, in the case of product use by females, the corrugated portion of the absorbent structure would be oriented closer to the center of the diaper. Dimensionally, the corrugated portion of the absorbent material will typically be greater than about 40 mm in width, greater than about 100 mm in length and comprise greater than about 5% of the product area.

Figure 4:
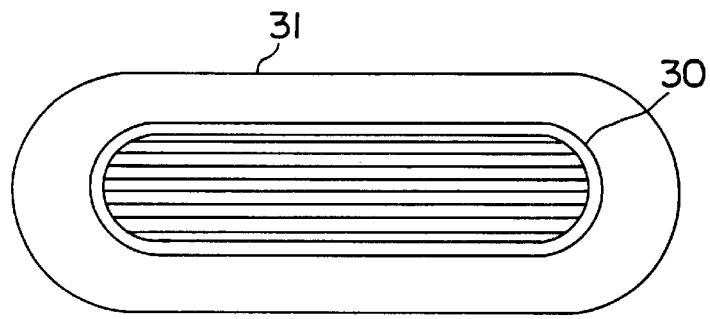
FIG. 4 is a diagram showing the use of the nonwoven corrugated material of this invention used as an airlaid intake/distribution strip as may be found in certain types of feminine care products.

Additional applications of the absorbent material of this invention may include corrugation of the airlaid fluid intake/distribution strip 30 found in some sanitary pads and napkins 31 as shown in FIG. 4. In this case, the corrugated airlaid material may enhance fluid handling by directing menses z-directionally into the core of the product, thereby providing improved cover desorption. In addition, the corrugations may provide reduced contact with the skin of the user, allowing for improved dryness. The corrugated absorbent layer may be used alone as long as it can provide the necessary fluid distribution functionality. However, it may also be used in conjunction with some type of distribution layer such as continuous fibers used for distribution in airlaid-tow composites.

Examples of corrugated materials are described in U.S. Pat. No. 4,111,733, U.S. Pat. No. 5,167,740, and U.S. Pat. No. 5,558,924, and are incorporated herein as reference. One example of modifying an absorbent core and fluid permeable top layer to produce a corrugated structure would be to feed the material through a nip having a doctor blade which reduces the speed of the web at the exit of the nip, thereby creating corrugations. Corrugations may also be produced using differential machine speeds. A third method for producing corrugations is through the use of an embossing roll having the desired pattern to achieve corrugations. Alternative methods to produce corrugated structures are feasible.

While in the foregoing specification this invention has been described in relation to certain desired embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An absorbent article comprising:
    a fluid permeable top sheet, a fluid impermeable back sheet, and a corrugated absorbent material having a plurality of alternating peaks and valleys disposed between said fluid permeable top sheet and said fluid impermeable back sheet;
    wherein the corrugated absorbent material has corrugations before and after wetting.

2. An absorbent article in accordance with claim 1, wherein said corrugated absorbent material has a base sheet basis weight in a range of about 50 gsm to about 900 gsm and a corrugated basis weight in a range of about 60 gsm to about 2250 gsm.

3. An absorbent article in accordance with claim 1, wherein said corrugated absorbent material comprises in a range of about 75% to about 98% by weight pulp and about 2% to about 25% by weight of a binder.

4. An absorbent article in accordance with claim 1, wherein said corrugated absorbent material comprises in a range of about 25% to about 93% by weight pulp, about 2% to about 25% by weight of a binder and about 0% to about 50% by weight of a superabsorbent.

5. An absorbent article in accordance with claim 1, wherein said corrugated absorbent material has a thickness in a range of about 0.3 mm to about 25 mm.

6. An absorbent article in accordance with claim 1, wherein said corrugated absorbent material comprises a nonwoven web of polymeric fibers.

7. An absorbent article in accordance with claim 1, wherein said fluid permeable top sheet is affixed to said corrugated absorbent material in a face-to-face relation by a method selected from the group consisting of thermal bonding, powder bonding, adhesive bonding, entanglement, ultrasonics and combinations thereof.

8. An absorbent article in accordance with claim 1, wherein said fluid permeable top sheet has been treated with a wettable surfactant.

9. An absorbent article in accordance with claim 1, wherein a nonwoven layer is disposed between said fluid permeable top sheet and said corrugated absorbent material.

10. An absorbent article in accordance with claim 9, wherein said nonwoven layer has been treated with a wettable surfactant so as to have a wettability greater than or equal to the wettability of said fluid permeable top sheet.

11. An absorbent article in accordance with claim 1, wherein said fluid permeable top sheet is a material selected from the group consisting of nonwoven webs, apertured films, hydroentangled webs, foams and combinations thereof.

12. An absorbent article in accordance with claim 1, wherein said alternating peaks and valleys have a cross direction orientation.

13. An absorbent article in accordance with claim 1, wherein said alternating peaks and valleys have a machine direction orientation.

14. An absorbent article in accordance with claim 1, wherein said corrugated absorbent material comprises at least one hydrophilic treatment disposed on at least one of said valleys.

15. An absorbent article in accordance with claim 1, wherein said corrugated absorbent material comprises at least one hydrophobic treatment disposed within at least one of said peaks.

16. An absorbent article in accordance with claim 1, wherein said corrugated absorbent material comprises structural means for providing resilience to said corrugated absorbent material.

17. An absorbent article in accordance with claim 16, wherein said structural means comprises a plurality of resilient fibers disposed in at least a portion of a surface of said corrugated absorbent material, an interior portion of said corrugated absorbent material, and combinations thereof.

18. An absorbent article in accordance with claim 1, wherein a frequency of said peaks and valleys is in a range of about 1 per 5 mm to about 1 per 25 mm of said corrugated absorbent material.

19. An absorbent article in accordance with claim 1, wherein said corrugated absorbent material comprises at least about 5% of a total product area of said absorbent article.

20. An absorbent article in accordance with claim 1, wherein said peaks and said valleys have a shape selected from the group consisting of rounded, plateau, triangular and combinations thereof.

21. An infant care product comprising:
    at least one corrugated absorbent material having a plurality of alternating peaks and valleys and having a base sheet basis weight in a range of about 35 gsm to about 900 gsm and a corrugated basis weight of about 60 gsm to about 2235 gsm;
    wherein the at least one corrugated absorbent material has corrugations before and after wetting.

22. An infant care product in accordance with claim 21 further comprising a fluid permeable top sheet affixed in a face-to-face relationship to said absorbent material and having a top sheet corrugation shape substantially corresponding to the absorbent material corrugation shape.

23. An infant care product in accordance with claim 22, wherein said fluid permeable top sheet is a material selected from the group consisting of nonwoven webs, apertured films, hydroentangled webs, foams and combinations thereof.

24. An infant care product in accordance with claim 22, wherein said fluid permeable top sheet has been treated to improve wettability.

25. An infant care product in accordance with claim 24, wherein said fluid permeable top sheet comprises at least one wettability gradient.

26. An infant care product in accordance with claim 22, wherein a nonwoven layer is disposed between said fluid permeable top sheet and said corrugated absorbent material.

27. An infant care product in accordance with claim 22, wherein a nonwoven layer is disposed between said fluid permeable top sheet and said corrugated absorbent material and has been treated with a wettable surfactant so as to have a wettability greater than or equal to the wettability of said fluid permeable top sheet.

28. An adult care product comprising:
    at least one corrugated absorbent material having a plurality of alternating peaks and valleys and having a base sheet basis weight in a range of about 35 gsm to about 900 gsm and a corrugated basis weight of about 60 gsm to about 2235 gsm;
    wherein the at least one corrugated absorbent material has corrugations before and after wetting.

29. An adult care product in accordance with claim 28 further comprising a fluid permeable top sheet affixed in a face-to-face relationship to said absorbent material and having a top sheet corrugation shape substantially corresponding to an absorbent material corrugation shape.

30. An adult care product in accordance with claim 28, wherein said fluid permeable top sheet is a material selected from the group consisting of nonwoven webs, apertured films, hydroentangled webs, foams and combinations thereof.

31. An adult care product in accordance with claim 28, wherein said fluid permeable top sheet has been treated to improve wettability.

32. An adult care product in accordance with claim 31, wherein said fluid permeable top sheet comprises at least one wettability gradient.

33. An adult care product in accordance with claim 28, wherein a nonwoven layer is disposed between said fluid permeable top sheet and said corrugated absorbent material.

34. An infant care product in accordance with claim 28, wherein a nonwoven layer is disposed between said fluid permeable top sheet and said corrugated absorbent material and has been treated with a wettable surfactant so as to have a wettability greater than or equal to the wettability of said fluid permeable top sheet.

35. A feminine care product comprising:
    at least one corrugated absorbent material having a plurality of alternating peaks and valleys and having a base sheet basis weight in a range of about 35 gsm to about 900 gsm and a corrugated basis weight of about 60 gsm to about 2235 gsm;
    wherein the at least one corrugated absorbent material has corrugations before and after wetting.

36. A feminine care product in accordance with claim 35 further comprising a fluid permeable top sheet affixed in a face-to-face relationship to said absorbent material and having a top sheet corrugation shape substantially corresponding to an absorbent material corrugation shape.

37. A feminine care product in accordance with claim 35, wherein said fluid permeable top sheet is a material selected from the group consisting of nonwoven webs, apertured films, hydroentangled webs, foams and combinations thereof.

38. A feminine care product in accordance with claim 35, wherein said fluid permeable top sheet has been treated to improve wettability.

39. A feminine care product in accordance with claim 38, wherein said fluid permeable top sheet comprises at least one wettability gradient.

40. A feminine care product in accordance with claim 35, wherein a nonwoven layer is disposed between said fluid permeable top sheet and said corrugated absorbent material.

41. A feminine care product in accordance with claim 35, wherein a nonwoven layer is disposed between said fluid permeable top sheet and said corrugated absorbent material and has been treated with a wettable surfactant so as to have a wettability greater than or equal to the wettability of said fluid permeable top sheet.

* * * * *